US00PP24050P3

(12) United States Plant Patent
Korlipara

(10) Patent No.: US PP24,050 P3
(45) Date of Patent: Nov. 26, 2013

(54) *AGASTACHE* PLANT NAMED 'BLUE BOA'

(50) Latin Name: ***Agastache* hybrid**
Varietal Denomination: Blue Boa

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 189 days.

(21) Appl. No.: 13/374,036

(22) Filed: Dec. 7, 2011

(65) Prior Publication Data

US 2013/0152260 P1 Jun. 13, 2013

(51) Int. Cl.
*A01H 5/00* (2006.01)

(52) U.S. Cl.
USPC ..... Plt./399

(58) Field of Classification Search
USPC ..... Plt./399
See application file for complete search history.

*Primary Examiner* — Kent L Bell

(74) *Attorney, Agent, or Firm* — Klarquist Sparkman, LLP

(57) ABSTRACT

A new and distinct form of *Agastache* plant characterized by deep purple blue flower, large inflorescences, a long bloom time, a stiffly upright, medium habit, and excellent vigor.

1 Drawing Sheet

Botanical denomination: *Agastache* hybrid.
Variety designation: 'Blue Boa'.

BACKGROUND OF THE INVENTION

The present invention relates to a new and distinct cultivar of *Agastache*, given the name, 'Blue Boa'. *Agastache* is in the family Lamiaceae. This new variety is a selection out of a breeding line using *Agastache rugosa* as a parent to provide hardiness and wet soil tolerance. This seedling was selected for its deep purple blue color and good habit. The exact parents are unknown.

Compared to *Agastache* 'Blue Fortune' and 'Black Adder', both unpatented plants, the new cultivar has deeper purple blue flower color, wider flower spikes, and a shorter habit.

This plant exhibits the following characteristics that make it unique:

1. deep purple blue flower,
2. large inflorescences,
3. a long bloom time,
4. a stiffly upright, medium habit,
5. and excellent vigor.

The new variety has been reproduced only by asexual propagation (stem cuttings and micropropagation using apical buds and nodes). Each of the progeny exhibits identical characteristics to the original plant. Asexual propagation by stem cuttings and micropropagation using apical buds and nodes as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a bed of five-month-old *Agastache* 'Blue Boa' growing in the field in late summer in Canby, Oreg.

DETAILED PLANT DESCRIPTION

The following is a detailed description of the new *Agastache* cultivar based on observations of five-month-old specimens in mid July (planted outside in the ground in May from greenhouse grown plants) in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, 5$^{th}$ edition.

Plant:

*Form*.—Upright.
*Type*.—Herbaceous perennial.
*Cold hardiness*.—USDA Zone 6-10.
*Size*.—Grows to 45 cm wide and 66 cm tall to the top of the flowers.
*Vigor*.—Excellent.
*Branching*.—About 8 main stems from the base, these branch at every node.
*Stem*.—Square in cross section, grows to 8 mm wide and 44 cm tall to the first flower, pubescent, internodes range from 2 to 10 cm long, Yellow Green 147B where herbaceous, where woody Brown 200B.
*Roots*.—White 155B, fibrous, plants root easily from stem tip cuttings.

Leaf:

*Type*.—Simple.
*Arrangement*.—Opposite.
*Shape*.—Ovate.
*Venation*.—Pinnate.
*Margins*.—Coarsely serrate.
*Apex*.—Acuminate.
*Base*.—Cordate.
*Blade size*.—Grows to 58 mm long and 40 mm wide.
*Surface texture*.—Pubescent on both sides.
*Petiole description*.—11 mm long and 1 mm wide, pubescent, Yellow Green 147C tinted Greyed Purple 187B in sun.
*Leaf color*.—Top side closest to Green 137A, bottom side closest to Yellow Green 147B.

Inflorescence:

*Type*.—Terminal spike with 8 to 12 whorls.
*Number of flowers*.—Up to 600 per spike.

*Size of inflorescence*.—Grows to 16 cm tall and 4 cm wide.

*Peduncle*.—Grows to 9 cm tall and 2 mm wide, pubescent, Yellow Green 147C tinted Greyed Purple 187A.

*Pedicel*.—Grows to 1 mm long, pubescent, Greyed Purple N187A.

*Bloom period*.—June through frost in Canby, Oreg.

Flower bud:

*Size*.—14 mm long and 3 mm wide at the widest point prior to opening.

*Description*.—Tubular.

*Surface texture*.—Pubescent.

*Color*.—Violet 83A.

Flower:

*Type*.—Zygomorphic.

*Shape*.—Bilabiate, tubular.

*Size*.—20 mm long and 7 mm wide.

*Corolla description*.—15 mm long and spreads to 7 mm wide; overall color outside Violet Blue 90A and inside Violet N88A; glabrous inside and pubescent outside, tube 11 mm long and 1 mm to 4 mm wide; 2 upper lobes joined 3 mm long and 2 mm wide, ovate, tips notched, margin entire; three lower lobes, two spreading sideways and curve down slightly, each 1.5 mm long and 2 mm wide, tip obtuse, margin entire; bottom lobe, reflexed, broadly obovate with the sides cupping inward, notched at the tip, margin entire, 4 mm wide and 2 mm deep.

*Calyx description*.—Campanulate, 7 mm long and 3 mm wide, pubescent outside and glabrous inside, 5 lobed, lobes ovate, 2.5 mm long, entire, acuminate, tube Greyed Purple N186C, lobes Violet 83A.

*Pistil description*.—19 mm long, ovary 1.5 mm long, Yellow Green 145D, style 17 mm long, Violet Blue 91A at the base to 90A below the stigma; stigma two-parted, 0.5 mm, Violet Blue 90A.

*Stamen description*.—4 in number, paired and exerted, top two 10 mm long and bottom two 8 mm long, filaments Violet Blue 90A, anthers 0.5 mm long, Violet 83A, pollen White NN155A in a moderate amount.

*Fragrance*.—Light herbal.

*Lastingness*.—A spike blooms for about 3 weeks on the plant.

Fruit/seed: 4 nutlets, 1 mm long, ovoid, Black 202A.

Pests and diseases: *Agastache* are known to be susceptible to downy mildew (*Peronospora*) and rust (*Puccinia*) in dry summer months. The new cultivar has no known resistances but has shown no problems in Canby, Oreg.

I claim:

1. A new and distinct cultivar of *Agastache* plant substantially as shown and described.

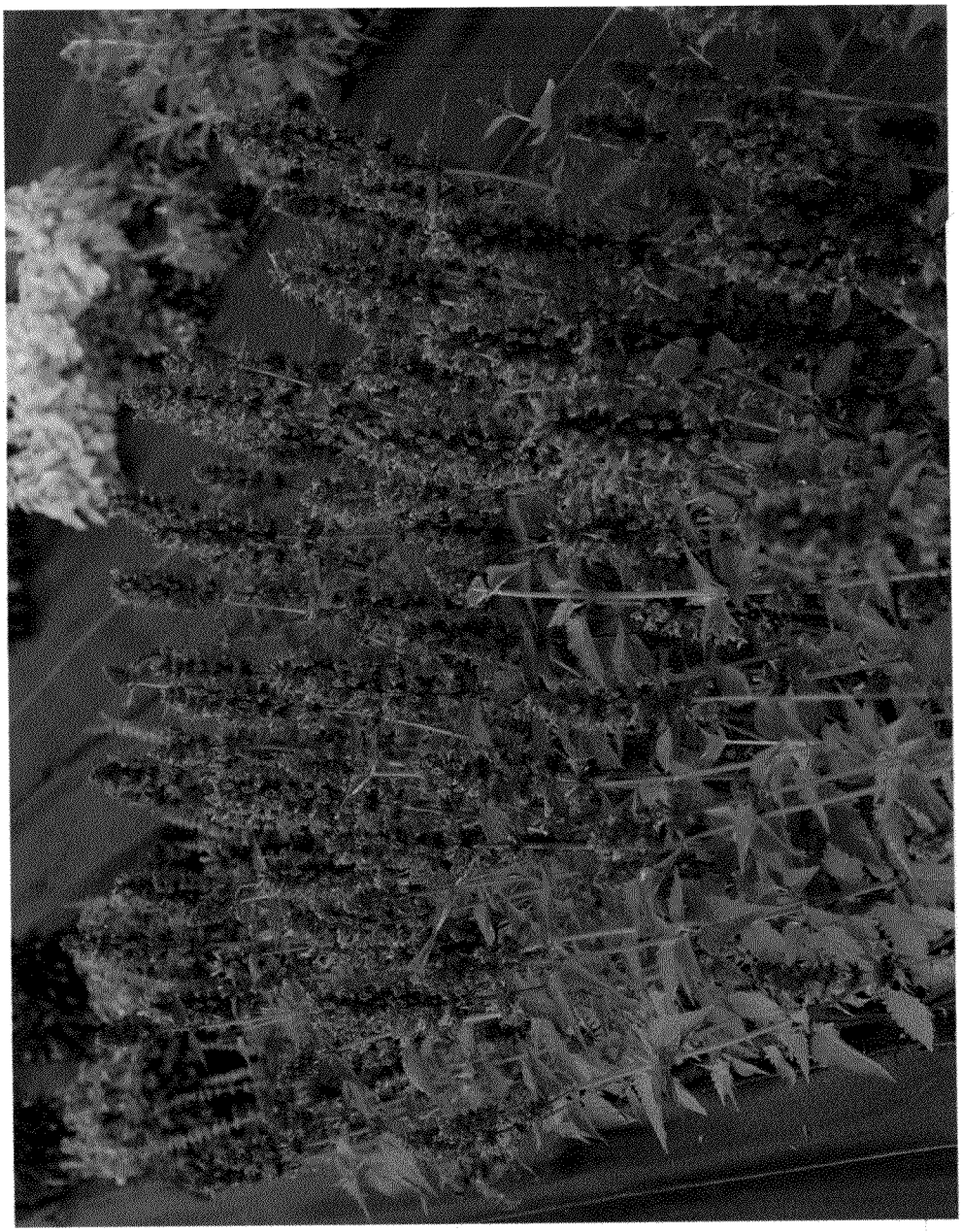

* * * * *